United States Patent [19]

Smeltz

[11] Patent Number: 4,958,038

[45] Date of Patent: Sep. 18, 1990

[54] ORGANOTITANIUM COMPOSITIONS USEFUL FOR CROSS-LINKING

[75] Inventor: Kenneth C. Smeltz, Wilmington, Del.

[73] Assignee: E. I. du Pont de Nemours and Company, Wilmington, Del.

[21] Appl. No.: 326,551

[22] Filed: Mar. 20, 1989

Related U.S. Application Data

[63] Continuation of Ser. No. 941,076, Dec. 8, 1986, abandoned.

[51] Int. Cl.$^5$ ................................................. C07F 7/28
[52] U.S. Cl. ...................................... 556/55; 252/8.551; 252/315.3; 536/17.1; 536/121
[58] Field of Search ................... 556/55; 536/121, 17.1

[56] References Cited

U.S. PATENT DOCUMENTS

| | | | |
|---|---|---|---|
| 2,898,356 | 8/1959 | Russell | 260/429.5 |
| 3,090,728 | 5/1963 | Berger | 556/55 |
| 3,460,956 | 8/1969 | Dahle | 556/55 |
| 3,888,312 | 6/1975 | Tiner et al. | 166/308 |
| 4,113,757 | 9/1978 | Kay | 556/55 |
| 4,609,479 | 9/1986 | Smeltz | 252/8.551 |

FOREIGN PATENT DOCUMENTS 195531  9/1986  European Pat. Off. .............. 556/55

*Primary Examiner*—Michael L. Shippen

[57] ABSTRACT

A process which comprises (A) combining (i) glycerol, erythritol, arabitol, xylitol, sorbitol, dulcitol, mannitol, inositol, a monosaccharide, or a disaccharide, (ii) water and (iii) lactic acid, glycolic acid, malic acid, citric acid, tartaric acid, saccharic acid, gluconic acid, glyceric acid or mandelic acid to provide an aqueous solution of the polyol and the α-hydroxy carboxylic acid, and (B) then at an alkaline pH of 10 or less reacting the solution with a tetravalent titanium compound of an inorganic acid at an α-hydroxy carboxylic acid:titanium mol ratio between about 0.5:1 and about 4:1 and a polyol:titanium mol ratio between about 0.25:1 and about 2:1.

32 Claims, No Drawings

ORGANOTITANIUM COMPOSITIONS USEFUL FOR CROSS-LINKING

This application is a continuation of application Ser. No. 06/941,076 filed Dec. 8, 1986, now abandoned.

SUMMARY OF THE INVENTION

The present invention relates to a novel process for preparing organic titanium compositions in which a tetravalent titanium compound of an inorganic acid is reacted with an alkaline aqueous solution containing an α-hydroxycarboxylic acid and a polyol. It relates also to the organotitanium compositions so formed. In addition, it relates to a process for hydraulically fracturing subterranean formations which involves the use of such organotitanium compositions as cross-linkers.

BACKGROUND OF THE INVENTION

Titanium esters react with high molecular weight hydroxyl-containing compounds so as to cross-link them and produce gels; J. Oil and Colour Chem. Assoc. 31, 405 (1948). However, simple alkyl titanates effect the cross-linking reaction at a rate that is too rapid for most industrial uses. The cross-linking reaction rate can be depressed by combining a titanium ester with a variety of multifunctional compounds. Examples of multifunctional compounds which have been reacted with simple alkyl esters of titanium include an α-hydroxycarboxylic acid in U.S. Pat. No. 2,870,181; 2,4-pentanedione or an acetoacetate in U.S. Pat. No. 2,680,108; and alkanolamines, such as triethanolamine, in U.S. Pat. No. 2,950,174 and 3,301,733.

Russell, in U.S. Pat. No. 2,898,356, disclosed that chelated titanium salts of α-hydroxy acids may be useful in the textile, leather and cosmetic industries, but that they may not be used at an alkaline pH. He proposed, therefore, a method for the preparation of a stabilized solution of such salts in alkaline aqueous media which comprises admixing a chelated titanium salt of an α-hydroxy acid with a polyol. He disclosed also that the chelated titanium salt of the α-hydroxy acid may be prepared by reacting an alkyl ester of ortho-titanic acid with an α-hydroxy acid or by reacting a titanium salt of an inorganic acid with an α-hydroxy acid. In the examples involving an inorganic titanium salt, Russell formed an aqueous solution of titanium tetrachloride or titanyl sulfate with sorbitol and then added malic or citric acid to it.

My U.S. Pat. No. 4,609,479 discloses and claims a process which comprises combining (i) a polyol selected from glycerol, erythritol, arabitol, xylitol, sorbitol, dulcitol, mannitol, inositol, monosaccharides, and disaccharides, (ii) water and (iii) an α-hydroxy carboxylic acid selected from lactic acid, glycolic acid, malic acid, citric acid, tartaric acid, saccharic acid, gluconic acid, glyceric acid and mandelic acid, and then reacting that combination of materials with a tetravalent titanium compound of an inorganic acid at an α-hydroxy carboxylic acid titanium mol ratio between about 1:1 and about 3:1 and a polyol:titanium mol ratio between about 0.25:1 and about 2:1.

The production of oil and gas can be stimulated by a technique, known as hydraulic (or fluid) fracturing, in which a fluid composition is introduced into an oil or gas well at a flow rate and pressure which create and/or extend a fracture into the oil- or gas-containing formation. The fluid composition usually carries a proppant (e.g., sand, bauxite, etc.) which is forced into the fracture by the fluid composition and prevents closure of the formation after the fluid pressure is released. For example, in my prior patent, described above, I disclosed using my aqueous reaction products in hydraulic fracturing. Earlier examples of fluid fracturing of oil and gas wells involved the use of: aqueous alcoholic solutions of natural gums which had been thickened by the use of inorganic alkali metal or alkaline earth metal salts in U.S. Pat. No. 3,634,237; hydratable polysaccharides cross-linked by $TiCl_4$ in U.S. Pat. No. 4,033,415; and solvatable polysaccharides cross-linked with ammonium tetralactotitanate(IV) or bis(triethanolamine)-bis(isopropyl)titanium in U.S. Pat. No. 3,888,312.

The process and the products of the present invention provide advantages over those of the prior art. The compositions of the present invention are more effective as cross-linkers than those of Russell. Moreover, the products of the present invention are prepared directly from a titanium salt, such as $TiCl_4$, thus eliminating the step of preparing the titanate commonly used in the prior art. In addition, the process and products of the present invention involve an aqueous medium, thereby avoiding flammmability and pollution problems associated with some of the prior art processes. The compositions of this invention are more effective in cross-linking high molecular weight hydroxyl-containing compositions at high temperatures (150°–300° F.) than are those of the prior art, including those of my prior patent described above. Furthermore, compositions of this invention give cross-linking results which are more reproducible than those of the prior art and which make more effective use of the Ti values. Also the process of this invention takes substantially less time to run than that of my prior patent.

DETAILED DESCRIPTION OF THE INVENTION

The manufacturing process of the present invention comprises combining a polyol, water and an α-hydroxy carboxylic acid, and then at an alkaline pH of 10 or less, reacting that combination of materials with a tetravalent titanium compound of an inorganic acid while maintaining the alkaline pH. In a preferred embodiment, the aqueous polyol/α-hydroxy carboxylic acid solution is brought to a pH between 8.2 and 9.5, most preferably 8.5±0.3, before any titanium compound is added to the solution. While said titanium compound is being added to said solution, the pH is usually maintained between 7.1 and 9, preferably between 8 and 8.8. The starting materials may be present at mol ratios in the range between about 0.5 and 4 mols of hydroxy acid per mol of titanium and between about 0.25 and 2 mols of polyol per mol of titanium. The process can be carried out at temperatures in the range from just above freezing to those in excess of 50° C. Preferably the process is run at a temperature in the range between about 20° C. and 30° C. In an embodiment, after reaction of the inorganic titanium compound with the aqueous polyol/acid solution, the product is heated to a temperature between about 50° C. and about 80° C. for between about 1 hour and 24 hours. Preferably, such postheating is conducted at a temperature between about 60° C. and about 80° C. for about 2 hours to about 4 hours. In another embodiment a material is added, with or without post-heating, which serves to stabilize the product of this invention; preferably sodium thiosulfate is used for that purpose.

The 60-hydroxy carboxylic acids useful according to the invention may be mononocarboxylic acids, such as lactic acid and glycolic acid; dicarboxylic acids, such as malic acid; or tricarboxylic acids, such as citric acid. Moreover, they can be polyhydroxypolycarboxylic acids such as tartaric acid or saccharic acid, monocarboxylic acids having a plurality of hydroxy groups, such as gluconic acid and glyceric acid, or aromatic hydroxy acids such as mandelic acid. The polyols also vary widely. In general, they are trihydric, tetrahydric, pentahydric or hexahydric alcohols, including glycerol, erythritol, arabitol, xylitol, sorbitol, dulcitol, mannitol, and inositol. Other polyols useful in the invention include monosaccharides, e.g., glucose, fructose, mannose, galactose and xylose, as well as disaccharides, such as sucrose, lactose, maltose and cellobiose. Sorbitol is the preferred polyol for purposes of the invention. Exemplary bases include sodium hydroxide, ammonium hydroxide and potassium hydroxide. Sodium hydroxide is preferred, particularly for a freeze-resistant composition having a water content in which the water:titanium mol ratio is between about 36:1 and about 60:1, most preferably between about 45:1 and 56:1.

In the hydraulic fracturing process of this invention, one or more fractures is created or extended in an oil- or gas-containing subterranean formation by introducing a cross-linked gel formed from a solvatable polysaccharide into the formation at a flow rate and pressure sufficient to create or extend such a fracture. The cross-linker consists essentially of one of the titanium compositions prepared in accordance with the method described above, preferably that prepared from $TiCl_4$, sorbitol, water and malic acid or lactic acid at a Ti:sorbitol:water:malic acid mol ratio of 1:0.67:52.5:1 or a Ti:sorbitol:water:lactic acid mol ratio of 1:0.5:47:1.

The solvatable polysaccharides include guar gum and locust bean gum, as well as other galactomannan and glucomannan gums, such as those derived from sennas, Brazilwood, Tera, Honey locust, Karaya gum and the like. Derivatives of such gums are useful also, e.g., hydroxyethylguar, hydroxypropylguar, carboxyethylhydroxyethylguar, carboxymethylhydroxypropylguar, and the like, as well as cellulose derivatives containing carboxyl groups, such as carboxymethylcellulose, carboxymethylhydroxyethylcellulose, and the like. Hydroxypropylguar and carboxymethylhydroxypropyl guar are preferred polysaccharides for use in the present invention. Hydroxypropylguar is the most preferred gum based upon its commercial availablity and desirable properties. On the other hand, carboxymethylhydroxypropylguar is sometimes used in place of hydroxypropylguar in fracturing fluids when the permeability of the formation is such that one wishes to keep the residual solids at a low level, so as to prevent formation damage. The solvatable polysaccharides can be used individually or in combination; usually, however, a single material is used. The solvatable polysaccharides are normally blended with a solvent such as water or an aqueous medium (e.g., aqueous methanol, ethanol, 1 to 3% HCl or potassium chloride) to form an uncrosslinkable gel as a first step.

The amounts of solvatable polysaccharide and the cross-linker therefor vary. One uses small but effective amounts which for both will vary with the circumstances, e.g., the type of geologic formation, the depth at which fluid fracturing is to be performed, temperature, pH, etc. Moreover, the type of cross-linker linker that is chosen will vary also with some of the same factors. In addition, their rates of cross-linking will be a factor to be considered in choosing the titanium compound. The aqueous titanium compounds of lactic and glycolic acids give approximately the same rates of cross-linking, with others in the following descending order: glycolic and lactic acids > malic acid > tartaric acid > citric acid > gluconic acid. In all cases, one uses as small an amount of each in water as will provide the viscosity level necessary to effect fracturing of the subterranean formation to the extent necessary to promote adequate recovery of oil or gas from it. For example, satisfactory gels can generally be made by using the solvatable polysaccharide in amounts up to about 1.5 weight percent and up to about 0.35 weight percent of the cross-linker, both percentages being based on the weight of the aqueous liquid. Preferably, from about 0.3 to to about 0.7 weight percent of the solvatable polysaccharide is used and from about 0.075 to about 0.15 weight percent of the cross-linker.

The following Examples are given in further illustration of the invention but not by way of limitation. Preparation of the compositions in the Examples were carried out in a closed vessel containing an agitator, pH probe, condenser, nitrogen inlet and dropping funnel. In Examples 1 and 2 (the best mode), a thermocouple was provided plus a recycle loop. In the other Examples, no recycle loop was used, and a thermometer was used in place of the thermocouple. Unless specified otherwise, percentages are given by weight, and temperatures are given in degrees Celsius.

EXAMPLE 1

D,1-malic acid (95.7 g, 0.71 mol) and sorbitol (86.7 g, 0.48 mol) were dissolved in tap water (257 g) and swept slowly with nitrogen. To this stirred solution, 30% aqueous NaOH was added dropwise at 25-28° until the pH was 8.6. $TiCl_4$ (135 g, 0.71 mol) was added dropwise simultaneously with 30% aqueous NaOH at 26 ±2° over a 4-hour period while the pH of the reaction mixture was maintained at 8.4 ± 0.4. Stirring was continued at 26 ± 2° for an additional 15 minutes. Recirculation was stopped and the material in the recycle loop was drained into the reaction vessel. The stirred reaction mixture was heated at 70° for 3 hours. After cooling to 30°, sodium thiosulfate pentahydrate (177.1 g, 0.71 mol) was added and recirculation through the recycle loop was again commenced while adjusting the pH to 8.2 ± 0.2. The light yellow product solution was filtered through two layers of #5 Whatman filter paper to give a solution weight 1322 g and containing 2.6% titanium.

EXAMPLE 2

Lactic acid (81.8 g of an 88.8% aqueous solution, 0.8 mol) and aqueous sorbitol (104.2 g of 70% solution, 0.4 mol) were dissolved in tap water (247.7 g) and swept slowly with nitrogen. To this stirred solution, 30% aqueous NaOH (89.3 g, 0.67 mol) was added dropwise at 26 ± 2° until the pH was 8.7. $TiCl_4$ (152.2 g, 0.8 mol) was added dropwise simultaneously with 30% aqueous NaOH at 26 ± 2° over a 2 hour and 30 minute period while the pH of the reaction mixture was maintained at 8.4 ± 0.4. Stirring was continued for an additional 15 minutes. The pH was adjusted to 8.2± 0.2. Recirculation was stopped and the recycle loop drained into the reaction vessel. The stirred reaction mixture was heated at 70° for 4 hours. After cooling to 30°, recirculation was again started and $Na_2S_2O_3 \cdot 5H_2O$ (198.6 g, 0.8 mol)

was added, and the pH was adjusted to 8.2 ± 0.2°. A total of 556.1 g (4.2 mols) of 30% aqueous NaOH was used (including the 0.67 mol used prior to the addition of TiCl$_4$). The product was a light yellow aqueous solution which weighed 1267.7 g and contained 2.9% titanium.

EXAMPLE 3

D,1-malic acid (40.2g, 0.3 mol) and sorbitol (54.6 g, 0.3 mol) were dissolved in deionized water (108 g) and swept slowly with nitrogen. At 25-26°, aqueous NaOH (29.6% solution) was added dropwise with stirring until the pH reached 10.6. TiCl$_4$ (57 g, 0.3 mol) was then added dropwise over a 54-minute period at 25-29° simultaneously with aqueous NaOH while the pH was allowed to drop slowly to 8.2. A total of 259.8 g (1.9 mols) of the 29.6% aqueous solution of NaOH (including that used initially to bring the pH to 10.6) were used. The product was an aqueous solution which weighed 519.6 g and contained 2.77% titanium. A portion of the product solution was heated with agitation at 70° for 120 minutes. On cooling to 25°, the pH was 8.1.

EXAMPLE 4

D,1-malic acid (201 g, 1.5 mols) and sorbitol (273 g, 1.5 mols) were dissolved in deionized water (540 g) and swept slowly with nitrogen. Aqueous NaOH (33.3% solution) was added dropwise with stirring at 24-25° until the pH reached 8.5. TiCl$_4$ (285 g, 1.5 mols) was added dropwise simultaneously with aqueous NaOH at 24-26° over a 95-minute period while the pH of the reaction mixture was maintained at 8.2-8.5. Stirring was continued for an additional 68 minutes at 5° while very small quantities of aqueous NaOH were added to maintain the pH at 8.2. The total 33.3% aqueous NaOH used for this Example was 1158.9 g (9.6 mols). The stirred reaction mixture was heated at 70° for 3 hours. After cooling to 30°, sodium thiosulfate pentahydrate (372 g, 1.5 mols) was added. The temperature dropped to 25° and the pH rose from 8.1 to 8.2. The product was a very pale yellow, slightly hazy aqueous solution which weighed 2824.7 g and contained 2.54% titanium.

EXAMPLE 5

D,1-malic acid (201 g, 1.5 mols) and sorbitol (205 g, 1.1 mols) were dissolved in deionized water (540 g) and swept slowly with nitrogen. To this stirred solution, 29.4% aqueous NaOH was added dropwise at 21-25° until the pH was 9.8. TiCl$_4$ (285 g, 1.5 mols) was added dropwise simultaneously with 29.4% aqueous NaOH at 24-26° over an 86-minute period while the pH of the reaction mixture was maintained at 8.2-8.7. Stirring was continued at 25° for an additional 20 minutes while very small quantities of aqueous NaOH were added to maintain the pH at 8.2. A total of 1279.2 g (9.4 mols) 29.4% aqueous NaOH was used. The stirred reaction mixture was heated at 70° for 3 hours. After cooling to 25°, sodium thiosulfate pentahydrate (372 g, 1.5 mols) was added resulting in endothermic dissolution. After warming the reaction mixture to 25°, the solution had a pH of 8.1. The product was a clear, light yellow aqueous solution which weighed 2877 g and contained 2.50% titanium.

EXAMPLE 6

D,1-malic acid (221.1 g, 1.65 mols) and sorbitol (150.2 g, 0.82 mol) were dissolved in deionized water (594 g) and swept slowly with nitrogen. To this stirred solution, 29.5% aqueous NaOH was added dropwise at 25-27° until the pH was 8.5. TiCl$_4$ (313.5 g, 1.65 mols) was added dropwise simultaneously with aqueous NaOH at 25-27° over a 75-minute period while the pH of the reaction mixture was maintained at 8.2-8.5. Stirring was continued at 25° for an additional 10 minutes while very small quantities of aqueous NaOH were added to maintain the pH at 8.2. The stirred reaction mixture was heated at 68-70° for 2.5 hours. After cooling to 30°, sodium thiosulfate pentahydrate (409.2 g, 1.65 mols) was added. Since the pH was 7.9, the solution was stirred at 25° for 15 minutes while small amounts of aqueous NaOH were added to bring the pH to 8.2. A total of 1385.1 g (10.2 mols) 29.5% aqueous NaOH was used. The product was a pale yellow, trace hazy, aqueous solution which weighed 3067 g and contained 2.58% titanium.

EXAMPLE 7

D,1-malic acid (804 g, 6 mols) and sorbitol (364 g, 2 mols) were dissolved in deionized water (2160 g) and swept slowly with nitrogen. To this stirred solution, 29.5% aqueous NaOH was added dropwise at 24-25° until the pH was 9.5. TiCl$_4$ (1140 g, 6 mols) was added dropwise simultaneously with aqueous NaOH at 25-27° over a 127-minute period while the pH of the reaction mixture was maintained at 8.2-8.5. Stirring was continued at 27° for an additional 10 minutes while very small quantities of aqueous NaOH were added to maintain the pH at 8.2. The stirred reaction mixture was heated at 70° for 3 hours. After cooling to 32°, sodium thiosulfate pentahydrate (1488 g, 6 mols) was added. Since the pH was 7.9 at 25°, small amounts of aqueous NaOH were added to the stirred solution to bring the pH to 8.2. A grand total of 5034.1 g (37 mols) of 29.5% aqueous NaOH was used. The product was a pale yellow, slightly hazy, aqueous solution which weighted 10,990 g and contained 2.62% titanium.

EXAMPLE 8

Lactic acid 88.1% aqueous (183.9 g, 1.8 mols) and sorbitol (163.8 g, 0.9 mol) were dissolved in deionized water (626.1 g) and swept slowly with nitrogen. To this stirred solution, 29.4% aqueous NaOH was added dropwise at 22-25° until the pH was 8.5. TiCl$_4$ (342 g, 1.8 mols) was added dropwise simultaneously with 29.4% aqueous NaOH at 23-25° over a 78-minute period while the pH of the reaction mixture was maintained at 8.1-8.5. Stirring was continued at 25° for an additional 35 minutes while very small quantities of aqueous NaOH were added to maintain the pH at 8.2. The stirred reaction mixture was heated at 70° for 3 hours. After cooling to 30°, sodium thiosulfate pentahydrate (446.4 g, 1.8 mols) was added. The pH of the mixture was increased from 7.4 to 8.2 by the addition of more aqueous NaOH. A total of 1224.5 g (9 mols) of 29.4% aqueous NaOH was used. The product was a clear, light yellow, aqueous solution which weighed 3017 g and contained 2.86% titanium.

EXAMPLE 9

Lactic acid 88.1% aqueous (613 g, 6 mols) and sorbitol (364 g, 2 mols) were dissolved in deionized water (2088 g) and swept slowly with nitrogen. To this stirred solution, 29.5% aqueous NaOH was added dropwise at 25-26° until the pH was 9.0. TiCl$_4$ (1140 g, 6 mols) was added dropwise simultaneously with aqueous NaOH at 24-25° - over a 145-minute period while the pH of the reaction mixture was maintained at 8.2–8.7. Stirring was continued at 27° for an additional 5 minutes while very small quantities of aqueous NaOH were added to maintain the pH at 8.2. The stirred reaction mixture was heated at 70° for 3 hours. After cooling to 40°, sodium thiosulfate pentahydrate (1488 g, 6 mols) was added. The pH of the mixture was increased from 7.4 to 8.2 at 25° by the addition of more aqueous NaOH. A total of 4193.9 g (30.9 mols) of aqueous NaOH was used. The product was a hazy, trace yellow, aqueous solution which weighed 9886.9 g and contained 2.88% titanium.

EXAMPLE 10

Lactic acid 88.1% aqueous (183.9 g, 1.8 mols) and sorbitol (81.9 g, 0.45 mol) were dissolved in deionized water (626.4 g) and swept slowly with nitrogen. To this stirred solution, 29.7% aqueous NaOH was added dropwise at 23–24° until the pH was 9.0. $TiCl_4$ (342 g, 1.8 mols) was added dropwise simultaneously with aqueous NaOH at 23–27° over a 73minute period while the pH of the reaction mixture was maintained at 8.2–8.8. Stirring was continued at 27° for an additional 12 minutes while very small quantities of aqueous NaOH were added to maintain the pH at 8.2. The stirred reaction mixture was heated at 70° for 3 hours. After cooling to 40°, sodium thiosulfate pentahydrate (446.4 g, 1.8 mols) was added. The pH of the mixture was increased from 7.4 to 8.2 at 25° by the addition of aqueous NaOH. A total of 1251.5 g (9.3 mols) of aqueous NaOH was used. The product was a trace hazy, colorless, aqueous solution which weighed 2932 g and contained 2.95% titanium.

I claim:

1. A process which comprises (A) combining (i) glycerol, erythritol, arabitol, xylitol, sorbitol, dulcitol, mannitol, inositol, a monosaccharide, or a disaccharide, (ii) water and (iii) lactic acid, glycolic acid, malic acid, citric acid, tartaric acid, saccharic acid, gluconic acid, glyceric acid or mandelic acid to provide an aqueous solution of the polyol and the α-hydroxy carboxylic acid, and (B) then at an alkaline pH of 10 or less reacting said solution with a tetravalent titanium compound of an inorganic acid at an α-hydroxy carboxylic acid:titanium mol ratio between about 0.5:1 and about 4:1 and a polyol:titanium mol ratio between about 0.25:1 and about 2:1.

2. The process of claim 1 wherein the pH of said aqueous solution is adjusted to a pH in the range between 8.2 and 9.5 before said titanium compound is added to said solution, and the pH is maintained in the range between 8 and 8.8 while said titanium compound is being added to said solution.

3. The process of claim 2 wherein the water content is such as to provide a water:titanium mol ratio between about 36:1 and 60:1.

4. The process of claim 2 wherein said acid is lactic acid, glycolic acid, malic acid, citric acid or tartaric acid.

5. The process of claim 2 wherein said polyol is glycerol, erythritol, arabitol, xylitol, sorbitol, dulcitol, mannitol, or myo-inositol.

6. The process of claim 2 wherein said polyol is sorbitol.

7. The process of claim 2 wherein said acid is lactic acid.

8. The process of claim 7 wherein said polyol is sorbitol.

9. The process of claim 8 wherein said titanium salt is $TiCl_4$.

10. The process of claim 9 wherein the pH of said aqueous solution is adjusted to a pH in the range between 8.2 and 8.8 before said $TiCl_4$ is added thereto and the pH is maintained at 8.4 ± 0.4 while $TiCl_4$ is being added to said solution.

11. The process of claim 10 wherein the mol ratio of lactic acid:sorbitol:titanium is 1:0.5:1.

12. The process of claim 2 wherein said acid is malic acid.

13. The process of claim 12 wherein said polyol is sorbitol.

14. The process of claim 13 wherein said salt is $TiCl_4$.

15. The process of claim 14 wherein the pH of said aqueous solution is adjusted to a pH in the range between 8.2 and 8.8 before said $TiCl_4$ is added thereto and the pH is maintained at 8.4 ± 0.4 while $TiCl_4$ is being added to said solution.

16. The process of claim 15 wherein the malic acid:sorbitol:titanium mol ratio is 1:0.67:1.

17. The composition produced in accordance with the process of claim 1.

18. The composition produced in accordance with the process of claim 2.

19. The composition produced in accordance with the process of claim 3.

20. The composition produced in accordance with the process of claim 4.

21. The composition produced in accordance with the process of claim 5.

22. The composition produced in accordance with the process of claim 6.

23. The composition produced in accordance with the process of claim 7.

24. The composition produced in accordance with the process of claim 8.

25. The composition produced in accordance with the process of claim 9.

26. The composition produced in accordance with the process of claim 10.

27. The composition produced in accordance with the process of claim 11.

28. The composition produced in accordance with the process of claim 12.

29. The composition produced in accordance with the process of claim 13.

30. The composition produced in accordance with the process of claim 14.

31. The composition produced in accordance with the process of claim 15.

32. The composition produced in accordance with the process of claim 16.

* * * * *